United States Patent
Zard et al.

Patent Number: 5,169,779
Date of Patent: Dec. 8, 1992

[54] PROCESS FOR THE PREPARATION OF METHYL (—)-(2R,3S)-2,3-EPOXY-3-(4-METHOXY-PHENYL)PROPIONATE

[75] Inventors: Lydia Zard, Gif-sur-Yvette; Arlette Tixidre, Orsay; Guy Rossey, Voisins le Bretonneux; Alexander Wick, St. Nom La Bretéche, all of France

[73] Assignee: Synthelabo, Paris, France

[21] Appl. No.: 654,518

[22] Filed: Feb. 13, 1991

[51] Int. Cl.$^5$ .............................................. C12P 41/00
[52] U.S. Cl. ................................... 435/280; 435/135
[58] Field of Search ................ 435/280, 197, 198, 135

[56] References Cited
FOREIGN PATENT DOCUMENTS
0362556  8/1989  European Pat. Off. .

OTHER PUBLICATIONS

Fitzpatrick et al., J. Am. Chem. Soc. 113:3166–3171 (1991).
Langrand et al., Tetrahedron Letters 27:29–32 (1986).

*Primary Examiner*—David M. Naff
*Assistant Examiner*—Sandra Saucier
*Attorney, Agent, or Firm*—Jacobson, Price, Holman & Stern

[57] ABSTRACT

A process for the preparation of methyl (—)-(2R,3S)-2,3-epoxy-3-(4-methoxyphenyl)propionate, which comprises subjecting the dextrorotatory (2S,3R) enantiomer, present in a starting mixture containing both the levorotatory (2R,3S and dextrorotatory (2S,3R) enantiomers, to a transesterification reaction, in an anhydrous medium and in the presence of an enzyme which does not affect the levorotatory (2R,3S) enantiomer. The latter is an intermediate for the synthesis of compounds such as Diltiazem.

14 Claims, No Drawings

PROCESS FOR THE PREPARATION OF METHYL (−)-(2R,3S)-2,3-EPOXY-3-(4-METHOXY-PHENYL)-PROPIONATE

The present invention is related with a process for the preparation of methyl (−)-(2R,3S)-2,3-epoxy-3-(4-methoxyphenyl)propionate of formula (I)

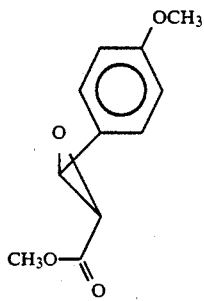

This compound is an important intermediate for the preparation of compounds such as (+)-(2S,3S)-3-acetyloxy-2,3-dihydro-5-(2-dimethylaminoethyl)-2-(4-methoxyphenyl)-1,5-5H-benzothiazepin-4-one, or Diltiazem (INN), and its derivatives.

The process of the invention is in fact a process of separation of the levorotatory (2R,3S) enantiomer from a mixture containing both enantiomers with the trans configuration, for example, the racemic mixture. It consists of a transesterification of the dextrorotatory (2S,3R) enantiomer, present in the starting mixture, in an anhydrous medium and in the presence of an enzyme which does not affect the levorotatory (2R,3S) enantiomer.

The methyl trans-(±)-2,3-epoxy-3-(4-methoxyphenyl)propionate, i.e. the racemic ester, is described in J. Chem. Soc., Perkin Trans. I, (1984), 1725.

The separation of the levorotatory enantiomer of methyl 2,3-epoxy-3-(4-methoxyphenyl)propionate from the racemic mixture in the presence of enzymes is described, for example, in patent applications such as EP-0343714, EP-0362556 and WO-90/04643.

The known methods involve reactions which are hydrolytic destructions of the dextrorotatory enantiomer, which do not affect the levorotatory enantiomer; their drawback is, that the hydrolysis products (substantially the free acid and decarboxylated products) remain in the reaction medium together with the desired levorotatory enantiomer. As a result of that, the modes of operation necessarily include liquid-liquid separation steps, extractions, etc, which are detrimental to the yield and purity of the final compound.

In contrast therewith, according to the present invention, the dextrorotatory enantiomer is converted into an insoluble derivative, which is easily eliminated from the reaction medium by simple filtration, the levorotatory enantiomer remaining in solution in the filtrate.

According to the invention, the transesterification agents are nucleophilic compounds, such as alcohols. It involves preferably aliphatic or alicyclic alcohols consisting of 2 to 12 carbon atoms, and operatically containing another functional group, such as acid, metal salt, ester, amine, alcohol, aminoacid, etc. It can also involve a polyol such as, for example, glycerol or glucose.

The preferred transesterification agents are alcohols containing a chain of 3 to 5 carbon atoms, particularly n-butanol and its derivatives, i.e. primary alcohols whose OH function is located at the end of a 4 carbon atom chain, said carbon atoms bearing optional substituents or forming part of a functional group such as acid, salt or ester.

A particularly interesting transesterification agent is an alkali-metal or alkaline-earth salt of 4-hydroxybutanoic acid, for example the sodium, potassium or calcium salt because, as well as the transesterification product, it is insoluble in the reaction medium.

The solvent to be employed must of course be inert for the enzyme; according to the invention it is a non-nucleophilic solvent selected from hydrocarbons, for example hexane, heptane, cyclohexane, benzene, toluene, xylenes; or from chlorinated solvents, for example, dichloromethane, chloroform, chlorobenzene, dichlorobenzenes; or from ethers, for example, diethyl ether, diisopropyl ether, t-butylmethyl ether; or from ketones, for example, methylisobutylketone.

The enzymes to be employed are lipases or esterases, preferably of the E.C.3.1.1 class. The preferred enzymes are those isolated from *Candida cylindracea, Alcaligenes, Mucor miehei* or the L.P.L. enzyme, from Pseudomonas, Amano Pharmaceutical Ltd.

These enzymes can be used as such or immobilized on an inert carrier, such as membranes.

The transesterification reaction occurs at a temperature ranging from 10° to 70° C., for example, at room temperature or, preferably, between 20° and 60° C. Its progress is monitored by high performance liquid chromatography (HPLC).

The following examples illustrate in detail typical experimental procedures according to the invention.

In said examples, the enantiomeric excess, ee, is defined as follows:

$$ee = \frac{[R] - [S]}{[R] + [S]} \times 100\%, \text{ wherein } [R] \text{ and } [S] \text{ are the concentrations of the two enantiomers).}$$

EXAMPLE 1

To a solution of 5 g of methyl trans-(±)-2,3-epoxy-3-(4-methoxyphenyl)propionate in 150 ml of toluene are added 2 g of lipase Alcaligenes and 4.6 g of 4-hydroxybutanoic acid sodium salt, and the reaction mixture is stirred at 37° C. for 40 h.

The reaction mixture is then filtered and the residue is rinsed with toluene.

The filtrate is evaporated under reduced pressure and the crystalline residue is taken up in t-butylmethyl ether at −10° C., leaving 2 g of white crystals of pure (−)-methyl (2R,3S)-2,3-epoxy-3-(4-methoxyphenyl)propionate.

mp: 86°-87° C.
$[\alpha]_D^{22} = -201°(c=1; \text{MeOH})$
ee=100% (CLHP)

EXAMPLE 2

To a solution of 2.5 g of methyl trans-(±)-2,3-epoxy-3-(4-methoxyphenyl)propionate in 100 ml of toluene are added 250 mg of lipase Candida cylindracea and 12 ml of n-butanol, and the reaction mixture is stirred at room temperature for 40 h. The reaction is followed by HPLC, and after the complete disappearance of the dextrorotatory enantiomer, the reaction mixture is poured into water and extracted with diethyl ether.

After drying over magnesium sulfate and evaporation of the solvent, 3 g of oily, residue are obtained, which crystallize on cooling at 5° C.

The crystals are rinsed with t-butylmethyl ether at −10° C., leaving 740 mg of pure (−)-methyl (2R,3S)-2,3-epoxy-3-(4-methoxyphenyl)propionate.

mp: 86°–87° C.

ee=100% (CLHP)

EXAMPLE 3

The method is performed as described in example 1, using various enzymes. After stirring for 20 h, the ratio between methyl (−)-(2R,3S)-2,3-epoxy-3-(4-methoxyphenyl)propionate and its dextrorotatory (not yet reacted) enantiomer in the reaction mixture is measured by HPLC.

The following table shows the enzymes used and, for each one, the ratio of the U. V. intensities (254 nm).

| Lipase | Ratio |
| --- | --- |
| Alcaligenes | 74/23 |
| Rhizopus arrhizus | 50/50 |
| Rhizopus delamar | 50/50 |
| Rhizopus japonicus | 50/50 |
| Candida cylindracea | 56/43 |
| Pseudomonas fluorescens | 50/50 |
| Candidum geotrichum | 50/50 |
| Aspergillus niger | 50/50 |
| Mucor miehei | 62/38 |
| Amano LPL | 52/48 |

We claim:

1. A process for the preparation of methyl (−)-(2R,3S)-2,3-epoxy-3-(4-methoxyphenyl)propionate, which comprises subjecting the dextrorotatory (2S,3R) enantiomer, present in a starting mixture containing both the levorotatory (2R,3S) and dextrorotatory (2S,3R) enantiomers, to a transesterification reaction performed with a derivative of n-butanol whose OH function is located at the end of a 4-carbon-atom chain, said carbon atoms bearing a substituent which is or forms part of a member selected from a functional group consisting of acid, salt and ester, in an anhydrous solvent medium and in the presence of an enzyme which catalyzes the transesterification of the dextrorotatory (2S,3R) enantiomer into a compound that is insoluble in the anhydrous solvent medium and which does not substantially react with the levorotatory (2R,3S) enantiomer, filtering the insoluble compound from the medium to obtain a filtrate, and evaporating the solvent from the filtrate.

2. A process according to claim 1, wherein said starting mixture is the racemic mixture.

3. A process according to claim 1, wherein the transesterification is performed with a alkali-metal or alkaline-earth-metal salt of 4-hydroxybutanoic acid.

4. A process according to claim 1, wherein the transesterification is performed with the 4-hydroxybutanoic acid sodium salt.

5. A process according to claim 1 wherein the transesterification is performed with an enzyme of the E.C.3.1.1 class.

6. A process according to claim 1, wherein the transesterification is performed with the lipase isolated from *Candida cylindracea*.

7. A process according to claim 1, wherein the transesterification is performed with the lipase isolated from Alcaligenes.

8. A process according to claim 1, wherein the transesterification is performed with the lipase isolated from *Mucor miehei*.

9. A process according to claim 1, wherein the transesterification is performed with the lipase isolated from Pseudomonas, Amano Pharmaceutical, Ltd.

10. A process according to claim 1, wherein the enzyme is used as such in the reaction medium.

11. A process according to claim 1, wherein the enzyme is immobilized on an inert carrier.

12. A process according to claim 1, wherein the solvent is a non-nucleophilic solvent.

13. A process according to claim 1, wherein the solvent is a member selected from the group consisting of hexane, heptane, cyclohexane, benzene, toluene, xylene, a dichlorobenzene, chloroform, chlorobenzene, dichlorobenzenes, diethyl ether, diisopropyl ether, t-butylmethyl ether and methylisobutylketone.

14. A process according to claim 1, wherein the solvent is toluene.

* * * * *